United States Patent
Lheureux et al.

(10) Patent No.: US 10,617,616 B2
(45) Date of Patent: *Apr. 14, 2020

(54) COSMETIC COMPOSITION COMPRISING A SALICYLIC ACID COMPOUND

(71) Applicant: L'OREAL, Paris (FR)

(72) Inventors: Eric Lheureux, Montgeron (FR); Patricia Pierre, Antony (FR)

(73) Assignee: L'OREAL, Paris (FR)

( * ) Notice: Subject to any disclaimer, the term of this patent is extended or adjusted under 35 U.S.C. 154(b) by 16 days.

This patent is subject to a terminal disclaimer.

(21) Appl. No.: 15/755,850

(22) PCT Filed: Aug. 26, 2016

(86) PCT No.: PCT/EP2016/070207
§ 371 (c)(1),
(2) Date: Feb. 27, 2018

(87) PCT Pub. No.: WO2017/036969
PCT Pub. Date: Mar. 9, 2017

(65) Prior Publication Data
US 2018/0325787 A1    Nov. 15, 2018

(30) Foreign Application Priority Data
Aug. 28, 2015   (FR) ..................... 15 58026

(51) Int. Cl.
| | | |
|---|---|---|
| *A61K 8/368* | (2006.01) | |
| *A61K 8/37* | (2006.01) | |
| *A61Q 19/00* | (2006.01) | |
| *A61K 8/81* | (2006.01) | |
| *A61K 8/86* | (2006.01) | |
| *A61K 8/06* | (2006.01) | |
| *A61K 8/39* | (2006.01) | |
| *A61Q 19/08* | (2006.01) | |

(52) U.S. Cl.
CPC .............. *A61K 8/368* (2013.01); *A61K 8/062* (2013.01); *A61K 8/375* (2013.01); *A61K 8/39* (2013.01); *A61K 8/8152* (2013.01); *A61K 8/8158* (2013.01); *A61K 8/86* (2013.01); *A61Q 19/00* (2013.01); *A61Q 19/08* (2013.01)

(58) Field of Classification Search
CPC ........ A61K 8/368; A61K 8/375; A61K 19/00; A61K 8/8152; A61K 8/8158; A61K 8/86; A61K 8/062; A61K 8/39; A61K 19/08
See application file for complete search history.

(56) References Cited

U.S. PATENT DOCUMENTS

2003/0108498 A1\* 6/2003 Stephens ................. A61K 8/89
424/63
2009/0232756 A1\* 9/2009 Monello ................ A61K 8/368
424/60

FOREIGN PATENT DOCUMENTS

| EP | 2 100 585 A1 | 9/2009 |
| FR | 2 951 084 A1 | 4/2011 |
| FR | 2 973 693 A1 | 10/2012 |
| FR | 3 000 670 A1 | 7/2014 |

\* cited by examiner

*Primary Examiner* — Shirley V Gembeh
(74) *Attorney, Agent, or Firm* — Polsinelli PC

(57) ABSTRACT

Cosmetic composition comprising a salicylic acid compound The invention relates to a composition in the form of an oil-in-water emulsion comprising: —a fatty acid ester of polyethylene glycol; —a $C1_6$-$C_{22}$ fatty acid ester of glycerol; —a polycondensate of ethylene oxide and of propylene oxide constituted of polyethylene glycol and polypropylene glycol blocks; —an at least partially neutralized acrylic acid homopolymer; —a 2-acrylamido-2-methylpropanesulfonic acid polymer; —a salicylic acid compound. The composition has good stability, in particular after 15 days of storage at 55° C. Use for caring for and making up keratin materials.

24 Claims, No Drawings

COSMETIC COMPOSITION COMPRISING A SALICYLIC ACID COMPOUND

CROSS REFERENCE TO RELATED APPLICATIONS

This application is a National Phase filing under 35 U.S.C. § 371 of PCT/EP2016/070207 filed on Aug. 26, 2016; and this application claims priority to Application No. 1558026 filed in France on Aug. 28, 2015 under 35 U.S.C. § 119. The entire contents of each application are hereby incorporated by reference.

The subject of the present invention is a cosmetic oil-in-water emulsion comprising a salicylic acid compound and a particular mixture of surfactant and gelling agents.

It is known practice to use salicylic acid and derivatives thereof in topical compositions, which are in particular cosmetic or dermatological, for example as a keratolytic agent for treating acne or as an anti-ageing agent. Documents FR-A-2 581 542 and EP-A-378 936 describe such derivatives.

However, the use of these compounds in oil-in-water emulsions containing a surfactant system comprising a fatty acid ester of polyethylene glycol and a $C_{16}$-$C_{22}$ fatty acid ester of glycerol has a tendency to destabilize the emulsion which then exhibits surface oil phase separation. The oil globules dispersed in the aqueous phase have a coarse appearance, rendering the emulsion non-homogeneous.

Application FR-A-292 8541 proposes stabilizing such emulsions with a polycondensate comprising ethylene oxide blocks and propylene oxide blocks.

However, it has been noted that, for fluid emulsions having a viscosity of less than 2.5 Pa·s (Poises) (measured under the conditions described hereinafter), in particular when they contain a sodium polyacrylate, these emulsions have insufficient stability after storage for 15 days at 55° C. The emulsion is not homogeneous when observed macroscopically (with the naked eye) and microscopically. This non-homogeneity makes the use of the emulsion by users totally unacceptable.

The objective of the present invention is therefore to provide a fluid emulsion containing salicylic acid or a derivative thereof and the surfactant system previously described, which is stable, in particular for 15 days at 55° C., or even for 2 months at 45° C.

The applicant has discovered that the stability of such an emulsion can be obtained with a gelling system comprising an at least partially neutralized acrylic acid homopolymer, such as sodium polyacrylate, and a 2-acrylamido-2-methyl-propanesulfonic acid polymer. The emulsion then has good homogeneity, both from the macroscopic point of view (with the naked eye) and from the microscopic point of view. It is also stable after a cycle of centrifugation at 900 G for 1 hour.

More specifically, a subject of the invention is a composition in the form of an oil-in-water emulsion comprising:
  a salicylic acid compound;
  a fatty acid ester of polyethylene glycol;
  a $C_{16}$-$C_{22}$ fatty acid ester of glycerol;
  a polycondensate of ethylene oxide and of propylene oxide;
  an at least partially neutralized acrylic acid homopolymer;
  a 2-acrylamido-2-methylpropanesulfonic acid polymer;
the composition having a viscosity, measured at 25° C., at a shear rate of 200 $min^{-1}$, of less than or equal to 2.5 Pa·s.

A subject of the invention is also a non-therapeutic process for caring for or making up keratin materials, comprising the application to the keratin materials of the composition as previously defined.

The salicylic acid compound present in the composition according to the invention is advantageously chosen from salicylic acid and the compounds of formula (I) below:

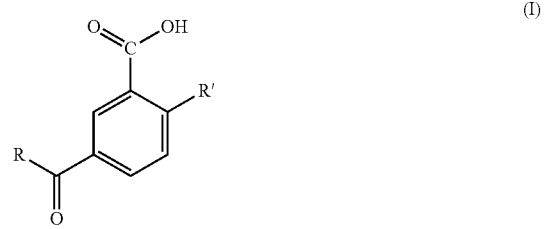

(I)

in which:
  the radical R denotes a linear, branched or cyclic, saturated aliphatic chain containing from 2 to 22 carbon atoms; an unsaturated chain containing from 2 to 22 carbon atoms containing one or more double bonds that may be conjugated; an aromatic nucleus linked to the carbonyl radical directly or via saturated or unsaturated aliphatic chains containing from 2 to 7 carbon atoms; said groups possibly being substituted with one or more substituents, which may be identical or different, chosen from (a) halogen atoms, (b) the trifluoromethyl group, (c) hydroxyl groups in free form or esterified with an acid containing from 1 to 6 carbon atoms, or (d) a carboxyl function in free form or esterified with a lower alcohol containing from 1 to 6 carbon atoms;
  R' is a hydroxyl group;
  and also salts thereof derived from an inorganic or organic base.

Preferentially, the radical R denotes a linear, branched or cyclic, saturated aliphatic chain containing from 3 to 11 carbon atoms; an unsaturated chain containing from 3 to 17 carbon atoms and comprising one or more conjugated or unconjugated double bonds; said hydrocarbon-based chains possibly being substituted with one or more substituents, which may be identical or different, chosen from (a) halogen atoms, (b) the trifluoromethyl group, (c) hydroxyl groups in free form or esterified with an acid containing from 1 to 6 carbon atoms, or (d) a carboxyl function in free form or esterified with a lower alcohol containing from 1 to 6 carbon atoms;
  and also salts thereof obtained by salification with an inorganic or organic base.

The compounds that are more particularly preferred are those in which the radical R is a $C_3$-$C_{11}$ alkyl group.

Among the compounds of formula (I) that are particularly preferred, mention may be made of:
5-n-octanoylsalicylic acid (or capryloylsalicylic acid); 5-n-decanoylsalicylic acid; 5-n-dodecanoyl-salicylic acid; 5-n-heptyloxysalicylic acid, and the corresponding salts thereof.

The salicylic acid compound is advantageously chosen from salicylic acid and 5-n-octanoylsalicylic acid.

The salts of the compounds of formula (I) may be obtained by salification with an inorganic or organic base. By way of example of an inorganic base, mention may be made of alkali metal or alkaline-earth metal hydroxides, for instance sodium hydroxide or potassium hydroxide, or aqueous ammonia.

Among the organic bases, mention may be made of amines and alkanolamines. Quaternary salts, for instance those described in patent FR 2 607 498, are particularly advantageous.

The compounds of formula (I) that may be used according to the invention are described in patents U.S. Pat. Nos. 6,159,479 and 5,558,871, FR 2 581 542, FR 2 607 498, U.S. Pat. No. 4,767,750, EP 378 936, U.S. Pat. Nos. 5,267,407, 5,667,789, 5,580,549 and EP-A-570 230.

The salicylic acid compound as previously described may be present in the emulsion according to the invention in a content ranging from 0.05% to 10% by weight, preferably ranging from 0.05% to 5% by weight and preferentially ranging from 0.1% to 3% by weight, relative to the total weight of the composition.

The composition according to the invention comprises, as principal emulsifying surfactant, at least one fatty acid ester of polyethylene glycol.

The fatty acid ester of polyethylene glycol present in the composition according to the invention is preferably a $C_{16}$-$C_{22}$ fatty acid ester comprising from 8 to 120 ethylene oxide units.

The fatty chain of the esters can be chosen in particular from the stearyl, behenyl, arachidyl, palmityl or cetyl units and mixtures thereof, such as cetearyl, and preferably a stearyl chain.

The number of ethylene oxide units may range from 8 to 120 and preferably from 20 to 120. According to one particular embodiment of the invention, this number may range from 50 to 120.

As examples of fatty acid esters of polyethylene glycol, mention may be made of stearic acid esters respectively comprising 20, 30, 40, 50 and 100 ethylene oxide units, such as the products respectively sold under the names Myrj 49 P (polyethylene glycol 20 EO stearate; CTFA name: PEG-20 stearate), Myrj 51, Myrj 52 P (polyethylene glycol 40 EO stearate; CTFA name: PEG-40 stearate), Myrj 53 and Myrj 59 P by the company Croda.

The fatty acid ester of polyethylene glycol may be present in the composition according to the invention in a content ranging from 0.1% to 10% by weight, preferably ranging from 0.1% to 5% by weight and preferentially ranging from 0.1% to 3% by weight, relative to the total weight of the composition.

The composition according to the invention also comprises an additional emulsifying surfactant chosen from $C_{16}$-$C_{22}$ fatty acid esters of glycerol.

The fatty acid ester of glycerol may be obtained in particular from an acid comprising a saturated linear alkyl chain containing from 16 to 22 carbon atoms. Fatty acid esters of glycerol that may in particular be mentioned include glyceryl stearate (glyceryl mono-, di- and/or tristearate) (CTFA name: Glyceryl stearate) or glyceryl ricinoleate, and mixtures thereof. Preferably, the fatty acid ester of glycerol used is chosen from glyceryl stearates.

The fatty acid ester of glycerol may be present in an amount ranging from 0.1% to 10% by weight, preferably ranging from 0.1% to 5% by weight and preferentially ranging from 0.1% to 3% by weight, relative to the total weight of the composition.

The composition of the invention may in particular be a mixture of glyceryl stearate and of polyethylene glycol 100 EO monostearate and in particular that comprising a 50/50 mixture sold under the name Arlacel 165 by the company Croda.

The composition according to the invention comprises a polycondensate of ethylene oxide and of propylene oxide, and more particularly a copolymer constituted of polyethylene glycol and polypropylene glycol blocks, for instance polyethylene glycol/polypropylene glycol/polyethylene glycol triblock polycondensates. These triblock polycondensates have, for example, the following chemical structure:

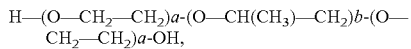

in which formula a ranges from 2 to 150 and b ranges from 1 to 100; preferably a ranges from 10 to 130 and b ranges from 20 to 80.

The polycondensate of ethylene oxide and of propylene oxide preferably has a weight-average molecular weight ranging from 1000 to 15000, better still ranging from 1500 to 15000, in particular ranging from 1500 to 10 000 and even better still ranging from 1500 to 5000.

Advantageously, said polycondensate of ethylene oxide and propylene oxide has a cloud point, at 10 g/l in distilled water, of greater than or equal to 20° C. and preferably of greater than or equal to 60° C. The cloud point is measured according to standard ISO 1065.

As polycondensates of ethylene oxide and propylene oxide that may be used according to the invention, mention may be made of the polyethylene glycol/polypropylene glycol/polyethylene glycol triblock polycondensates sold under the name Synperonic, for instance Synperonic® PE/F32 (INCI name: Poloxamer 108), Synperonic® PE/F108 (INCI name: Poloxamer 338), Synperonic® PE/L44 (INCI name: Poloxamer 124), Synperonic® PE/L42 (INCI name: Poloxamer 122), Synperonic® PE/F127 (INCI name: Poloxamer 407), Synperonic® PE/F88 (INCI name: Poloxamer 238), Synperonic® PE/L64 (INCI name: Poloxamer 184) by the company Croda, or else Lutrol® F68 (INCI name: Poloxamer 188) by the company BASF.

The polycondensate of ethylene oxide and propylene oxide may be present in the composition according to the invention in a content ranging from 0.01% to 5% by weight, preferably ranging from 0.05% to 3% by weight and preferentially ranging from 0.05% to 1% by weight, relative to the total weight of the composition.

The composition according to the invention contains an at least partially neutralized acrylic acid homopolymer.

The acrylic acid homopolymer is advantageously present in the composition in a non-particulate form.

The homopolymer used according to the invention is in particular chosen from sodium polyacrylates and potassium polyacrylates. Sodium polyacrylate is preferably used.

The acrylic acid homopolymer may be advantageously neutralized to a degree ranging from 5% to 80%.

As sodium polyacrylate that can be used according to the invention, use may be made of those sold under the names Cosmedia SP® or Cosmedia SPL® by the company Cognis, or else Luvigel® EM sold by the company BASF.

The at least partially neutralized acrylic acid homopolymer may be present in the composition according to the invention in a content ranging from 0.05% to 1% by weight, relative to the total weight of the composition, and preferably ranging from 0.1% to 0.5% by weight.

The composition according to the invention comprises a homopolymer of a monomer comprising a sulfonic group.

The polymers comprising at least one monomer comprising a sulfonic group that are used in the composition of the invention are advantageously water-soluble or water-dispersible or water-swellable. The polymers used in accordance with the invention are homopolymers that may be obtained from at least one ethylenically unsaturated monomer bearing a sulfonic group, which may be in free form or partially or totally neutralized.

Preferentially, the polymers in accordance with the invention may be partially or totally neutralized with an inorganic base (sodium hydroxide, potassium hydroxide or aqueous ammonia) or an organic base such as monoethanolamine, diethanolamine or triethanolamine, an aminomethylpropanediol, N-methylglucamine, basic amino acids, for instance arginine and lysine, and mixtures of these compounds. They are generally neutralized. In the present invention, the term "neutralized" is intended to mean polymers that are totally or virtually totally neutralized, i.e. at least 90% neutralized.

The polymers used in the composition of the invention generally have a number-average molecular weight ranging from 1000 to 20000000 g/mol, preferably ranging from 20 000 to 5000000 g/mol and even more preferentially from 100 000 to 1500000 g/mol.

These polymers according to the invention may be crosslinked or non-crosslinked.

The monomers comprising a sulfonic group of the polymer used in the composition of the invention are in particular chosen from vinylsulfonic acid, styrenesulfonic acid, (meth)acrylamido($C_1$-$C_{22}$)alkylsulfonic acids, N—($C_1$-$C_{22}$)alkyl (meth)acrylamido($C_1$-$C_{22}$)alkylsulfonic acids such as undecylacrylamidomethanesulfonic acid, and also partially or totally neutralized forms thereof, and mixtures thereof.

According to a preferred embodiment of the invention, the monomers comprising a sulfonic group are chosen from (meth)acrylamido($C_1$-$C_{22}$)alkylsulfonic acids, for instance acrylamidomethanesulfonic acid, acrylamidoethanesulfonic acid, acrylamidopropanesulfonic acid, 2-acrylamido-2-methylpropanesulfonic acid, 2-methacrylamido-2-methylpropanesulfonic acid, 2-acrylamido-n-butanesulfonic acid, 2-acrylamido-2,4,4-trimethylpentanesulfonic acid, 2-methacrylamidododecylsulfonic acid and 2-acrylamido-2,6-dimethyl-3-heptanesulfonic acid, and also partially or totally neutralized forms thereof, and mixtures thereof.

More particularly, use is made of 2-acrylamido-2-methylpropanesulfonic acid (AMPS), and also partially or totally neutralized forms thereof.

When the polymers are crosslinked, the crosslinking agents may be chosen from the polyolefinically unsaturated compounds commonly used for crosslinking polymers obtained by radical polymerization.

Examples of crosslinking agents that may be mentioned include divinylbenzene, diallyl ether, dipropylene glycol diallyl ether, polyglycol diallyl ethers, triethylene glycol divinyl ether, hydroquinone diallyl ether, ethylene glycol or tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl (meth)acrylate, allylic ethers of alcohols of the sugar series, or other allyl or vinyl ethers of polyfunctional alcohols, and also the allylic esters of phosphoric and/or vinylphosphonic acid derivatives, or mixtures of these compounds.

According to one preferred embodiment of the invention, the crosslinking agent is chosen from methylenebisacrylamide, allyl methacrylate and trimethylolpropane triacrylate (TMPTA). The degree of crosslinking generally ranges from 0.01 mol % to 10 mol % and more particularly from 0.2 mol % to 2 mol % relative to the polymer.

The homopolymer of monomers comprising a sulfonic group may be crosslinked with one or more crosslinking agents.

These homopolymers are generally crosslinked and neutralized, and they may be obtained according to the preparation process comprising the following steps:

(a) the monomer such as 2-acrylamido-2-methylpropanesulfonic acid in free form is dispersed or dissolved in a solution of tert-butanol or of water and tert-butanol;
(b) the monomer solution or dispersion obtained in (a) is neutralized with one or more inorganic or organic bases, preferably aqueous ammonia $NH_3$, in an amount making it possible to obtain a degree of neutralization of the sulfonic acid functions of the polymer ranging from 90% to 100%;
(c) the crosslinking monomer(s) is (are) added to the solution or dispersion obtained in (b);
(d) a standard free-radical polymerization is performed in the presence of free-radical initiators at a temperature ranging from 10 to 150° C.; the polymer precipitates in the tert-butanol-based solution or dispersion.

The preferred AMPS homopolymers are generally characterized in that they comprise, randomly distributed:
a) from 90% to 99.9% by weight of units of general formula (II) below:

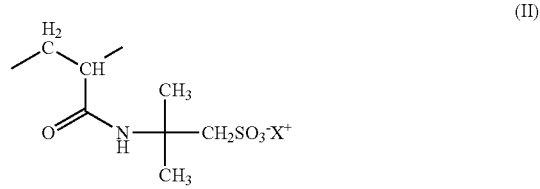

(II)

in which $X^+$ denotes a proton, an alkali metal cation, an alkaline-earth metal cation or the ammonium ion, not more than 10 mol % of the cations $X^+$ possibly being protons $H^+$;
b) from 0.01% to 10% by weight of crosslinking units originating from at least one monomer containing at least two olefinic double bonds; the weight proportions being defined relative to the total weight of the polymer.

The homopolymers according to the invention that are more particularly preferred comprise from 98% to 99.5% by weight of units of formula (II) and from 0.2% to 2% by weight of crosslinking units.

A polymer of this type that may in particular be mentioned is the crosslinked and neutralized 2-acrylamido-2-methylpropanesulfonic acid homopolymer sold by the company Clariant under the trade name Hostacerin® AMPS (CTFA name: ammonium polyacryldimethyltauramide).

The homopolymer of a monomer comprising a sulfonic group may be present in the composition according to the invention in a content ranging from 0.1% to 3% by weight, preferably ranging from 0.1% to 2% by weight, preferentially ranging from 0.5% to 2% by weight, relative to the total weight of the composition.

The composition according to the invention may comprise an additional hydrophilic gelling agent for thickening the aqueous phase of the composition.

The hydrophilic gelling agent may be chosen, for example, from:
(i) carboxyvinyl polymers (for instance optionally crosslinked acrylic acid polymers), such as the products sold under the names Carbopol (INCI name: Carbomer) by the company Goodrich;
(ii) polyacrylamides and 2-acrylamido-2-methylpropanesulfonic acid polymers and copolymers, optionally crosslinked and/or neutralized, for instance the poly(2-acrylamido-2-methylpropanesulfonic acid) sold by the company Hoechst under the name Hostacerin AMPS (INCI name: ammonium polyacryloyldimethyltaurate); crosslinked anionic copolymers of acrylamide and of AMPS, which are in the form of an emulsion, such as those sold under the name Sepigel 305 (CTFA name: Polyacrylamide/$C_{13}$-$C_{14}$ Isoparaffin/Laureth-7) and under the name Simulgel 600 (CTFA name: Acrylamide/sodium acryloyldimethyltaurate copolymer/isohexadecane/polysorbate 80) by the company SEPPIC; crosslinked anionic copolymers of acrylic acid and of AMPS, which are in the form of an emulsion, such as those sold under the name Simulgel EG (CTFA name: Sodium acrylate/sodium acryloyldimethyltaurate copolymer/isohexadecane/Polysorbate 80);

(iii) polysaccharides such as xanthan gums, guar gums, alginates, and cellulose polymers, for instance hydroxyethylcellulose, hydroxypropylcellulose and carboxymethylcellulose;

(iv) inorganic compounds such as modified or unmodified smectites and hectorites, such as the Bentone products sold by the company Rheox, the Laponite products sold by the company Southern Clay Products, and the product Veegum HS sold by the company R.T. Vanderbilt; and mixtures thereof.

Among these hydrophilic gelling agents, xanthan gum will more particularly be chosen.

The additional hydrophilic gelling agent may be present in the composition according to the invention in a content ranging from 0.01% to 3% by weight, relative to the total weight of the composition, preferably ranging from 0.1% to 1% by weight and preferentially ranging from 0.1% to 0.5% by weight.

The composition according to the invention comprises an aqueous phase.

The composition may comprise water in a content ranging from 40% to 95% by weight, preferably ranging from 50% to 90% by weight and preferentially ranging from 55% to 80% by weight, relative to the total weight of the composition.

The water may be a floral water such as cornflower water and/or a mineral water such as Vittel water, Lucas water or La Roche Posay water and/or a spring water.

The composition may also comprise an organic solvent that is water-miscible at ambient temperature (25° C.), chosen in particular from monoalcohols containing from 2 to 6 carbon atoms, such as ethanol or isopropanol;

polyols in particular containing from 2 to 20 carbon atoms, preferably containing from 2 to 10 carbon atoms and preferentially containing from 2 to 6 carbon atoms, such as glycerol, propylene glycol, butylene glycol, pentylene glycol, hexylene glycol, dipropylene glycol or diethylene glycol;

glycol ethers (in particular containing from 3 to 16 carbon atoms) such as mono-, di- or tripropylene glycol ($C_1$-$C_4$) alkyl ethers, and mono-, di- or triethylene glycol ($C_1$-$C_4$) alkyl ethers;

and mixtures thereof.

The composition according to the invention may comprise an organic solvent that is miscible with water at ambient temperature, in particular a polyol, in a content ranging from 1% to 20% by weight and preferably ranging from 3% to 15% by weight relative to the total weight of the composition.

Advantageously, the composition according to the invention has a pH ranging from 3.0 to 8.0, preferably ranging from 4.0 to 8.0, preferentially ranging from 4.5 to 6.5 and more preferentially ranging from 5.0 to 6.0.

The emulsion according to the invention also comprises an oily phase. The emulsion comprises at least one oil.

As oils that may more particularly be used in the composition of the invention, examples that may be mentioned include:

hydrocarbon-based oils of animal origin, such as perhydrosqualene (or squalane);

synthetic esters and ethers, in particular of fatty acids, for instance the oils of formulae $R^1COOR^2$ and $R^1OR^2$ in which $R^1$ represents a fatty acid residue containing from 8 to 29 carbon atoms, and $R^2$ represents a branched or unbranched hydrocarbon-based chain containing from 3 to 30 carbon atoms, for instance purcellin oil, isononyl isononanoate, isopropyl myristate, 2-ethylhexyl palmitate, 2-octyldodecyl stearate, 2-octyldodecyl erucate or isostearyl isostearate; hydroxylated esters, for instance isostearyl lactate, octyl hydroxystearate, octyldodecyl hydroxystearate, diisostearyl malate, triisocetyl citrate, and fatty alcohol heptanoates, octanoates and decanoates; polyol esters, for instance propylene glycol dioctanoate, neopentyl glycol diheptanoate and diethylene glycol diisononanoate; pentaerythritol esters, for instance pentaerythrityl tetraisostearate; and lipophilic amino acid derivatives, such as isopropyl lauroyl sarcosinate (INCI name: Isopropyl Lauroyl sarcosinate) sold under the name Eldew SL 205 by the company Ajinomoto;

linear or branched hydrocarbons, of mineral or synthetic origin, such as mineral oils (mixture of hydrocarbon-based oils derived from petroleum; INCI name: Mineral oil), volatile or non-volatile liquid paraffins, and derivatives thereof, petroleum jelly, polydecenes, isohexadecane, isododecane, hydrogenated isoparaffin such as Parleam® oil sold by the company NOF Corporation (INCI name: Hydrogenated Polyisobutene);

silicone oils, for instance volatile or non-volatile polymethylsiloxanes (PDMS) bearing a linear or cyclic silicone chain, which are liquid or pasty at ambient temperature, in particular cyclopolydimethylsiloxanes (cyclomethicones) such as cyclopentasiloxane and cyclohexadimethylsiloxane; polydimethylsiloxanes comprising alkyl, alkoxy or phenyl groups, which are pendent or at the end of a silicone chain, these groups containing from 2 to 24 carbon atoms; phenylsilicones, for instance phenyl trimethicones, phenyl dimethicones, phenyltrimethylsiloxydiphenylsiloxanes, diphenyl dimethicones, diphenylmethyldiphenyltrisiloxanes or 2-phenylethyl trimethylsiloxy silicates, and polymethylphenylsiloxanes;

fluoro oils, such as those which are partially hydrocarbon-based and/or silicone-based, for instance those described in document JP-A-2 295 912;

ethers such as dicapryl ether (CTFA name: Dicaprylyl ether); and $C_{12}$-$C_{15}$ fatty alkyl benzoates (Finsolv TN from Finetex);

mixtures thereof.

The oil may be present in the composition according to the invention in a content ranging from 1% to 50% by weight, relative to the total weight of the composition, preferably ranging from 5% 40% by weight, preferentially ranging from 5% to 30% by weight, and more preferentially ranging from 5% to 20% by weight.

The composition according to the invention may comprise at least one non-emulsifying crosslinked organopolysiloxane elastomer (also referred to as crosslinked silicone elastomer).

In particular, the non-emulsifying crosslinked organopolysiloxane elastomer used according to the invention is in the form of non-spherical particles.

For the purposes of the present invention, the term "non-emulsifying" silicone elastomer is intended to mean organopolysiloxane elastomers that do not contain a hydrophilic chain, such as polyoxyalkylene or polyglycerol units.

The non-emulsifying crosslinked silicone elastomer is a crosslinked organopolysiloxane elastomer that may be obtained:
- by a crosslinking addition reaction of a diorganopolysiloxane containing at least one hydrogen bonded to silicon and of a diorganopolysiloxane containing ethylenically unsaturated groups bonded to silicon, in particular in the presence of a platinum catalyst; or
- by a dehydrogenation crosslinking condensation reaction between a hydroxyl-terminated diorganopolysiloxane and a diorganopolysiloxane containing at least one hydrogen bonded to silicon, in particular in the presence of an organotin; or
- by a crosslinking condensation reaction of a hydroxyl-terminated diorganopolysiloxane and of a hydrolysable organopolysilane; or
- by thermal crosslinking of an organopolysiloxane, in particular in the presence of an organoperoxide catalyst; or
- by crosslinking of an organopolysiloxane with high-energy radiation such as gamma rays, ultraviolet rays or an electron beam.

Preferably, the crosslinked organopolysiloxane elastomer is obtained by a crosslinking addition reaction (A2) of a diorganopolysiloxane containing at least two hydrogens each bonded to a silicon, and (B2) of a diorganopolysiloxane containing at least two ethylenically unsaturated groups bonded to silicon, in particular in the presence (C2) of a platinum catalyst, for instance as described in application EP-A-295 886.

In particular, the organopolysiloxane may be obtained by reaction of dimethylvinylsiloxy-terminated dimethylpolysiloxane and of trimethylsiloxy-terminated methylhydropolysiloxane, in the presence of a platinum catalyst.

Compound (A2) is the base reactant for the formation of an organopolysiloxane elastomer and the crosslinking takes place via an addition reaction of compound (A2) with compound (B2) in the presence of the catalyst (C2).

Compound (A2) is advantageously a diorganopolysiloxane containing at least two lower (for example of $C_2$-$C_4$) alkenyl groups; the lower alkenyl group may be chosen from vinyl, allyl and propenyl groups. These lower alkenyl groups may be located at any position on the organopolysiloxane molecule but are preferably located at the ends of the organopolysiloxane molecule. The organopolysiloxane (A2) may have a branched chain, linear chain, cyclic or network structure, but the linear chain structure is preferred. Compound (A2) may have a viscosity ranging from the liquid state to the gum state. Preferably, compound (A2) has a viscosity of at least 100 centistokes at 25° C.

The organopolysiloxanes (A2) may be chosen from methylvinylsiloxanes, methylvinylsiloxane/dimethylsiloxane copolymers, dimethylvinylsiloxy-terminated dimethylpolysiloxanes, dimethylvinylsiloxy-terminated dimethylsiloxane/methylphenylsiloxane copolymers, dimethylvinylsiloxy-terminated dimethylsiloxane/diphenyl-siloxane/methylvinylsiloxane copolymers, trimethylsiloxy-terminated dimethylsiloxane/methylvinylsiloxane copolymers, trimethylsiloxy-terminated dimethylsiloxane/methylphenylsiloxane/methylvinylsiloxane copolymers, dimethylvinylsiloxy-terminated methyl(3,3,3-trifluoropropyl)polysiloxanes and dimethylvinylsiloxy-terminated dimethylsiloxane/methyl(3,3,3-trifluoropropyl)siloxane copolymers.

Compound (B2) is in particular an organopolysiloxane containing at least 2 hydrogens bonded to silicon in each molecule and is thus the crosslinking agent for compound (A2). Advantageously, the sum of the number of ethylenic groups per molecule in compound (A2) and the number of hydrogen atoms bonded to silicon per molecule in compound (B2) is at least 4.

Compound (B2) may be in any molecular structure, in particular in a linear chain, branched chain or cyclic structure.

Compound (B2) may have a viscosity at 25° C. ranging from 1 to 50 000 centistokes, in particular so as to be well miscible with compound (A).

It is advantageous for compound (B2) to be added in an amount such that the molecular ratio between the total amount of hydrogen atoms bonded to silicon in compound (B2) and the total amount of all the ethylenically unsaturated groups in compound (A2) is in the range from 1/1 to 20/1.

Compound (B2) may be chosen from trimethylsiloxy-terminated methylhydropolysiloxanes, trimethylsiloxy-terminated dimethylsiloxane/methylhydrosiloxane copolymers and dimethylsiloxane/methylhydrosiloxane cyclic copolymers.

Compound (C2) is the catalyst for the crosslinking reaction, and is in particular chloroplatinic acid, chloroplatinic acid-olefin complexes, chloroplatinic acid-alkenylsiloxane complexes, chloroplatinic acid-diketone complexes, platinum black and platinum on a support.

The catalyst (C2) is preferably added in an amount of from 0.1 to 1000 parts by weight and better still from 1 to 100 parts by weight, as clean platinum metal, per 1000 parts by weight of the total amount of compounds (A2) and (B2).

Other organic groups may be bonded to silicon in the organopolysiloxanes (A2) and (B2) described previously, for instance alkyl groups such as methyl, ethyl, propyl, butyl or octyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

According to one preferred embodiment, the non-emulsifying crosslinked silicone elastomer is generally mixed with at least one hydrocarbon-based oil and/or silicone oil to form a gel. In these gels, the non-emulsifying elastomer is in the form of non-spherical particles.

According to one particular mode, the non-emulsifying crosslinked silicone elastomer according to the invention is mixed with at least one volatile silicone oil, such as that defined hereinbelow as carrier.

Non-emulsifying elastomers are in particular described in patents U.S. Pat. Nos. 4,970,252, 4,987,169, 5,412,004, 5,654,362, 5,760,116 5,599,533 and 6,027,738 and in application JP-A-61-194 009.

According to one preferred mode, the non-emulsifying crosslinked silicone elastomer used in the present invention may be chosen from Dimethicone Crosspolymers (INCI name) and Dimethicone/Vinyl Dimethicone Crosspolymers (INCI name).

Non-emulsifying elastomers that may be used include those sold under the names KSG-6, KSG-15, KSG-16, KSG-18, KSG-41, KSG-42, KSG-43, KSG-44, USG-105 and USG-106 by the company Shin-Etsu, DC 9040, DC9041, DC9045, DC 9509, DC9505 and DC 9506 by the company Dow Corning, Gransil by the company Grant Industries, and SFE 839 by the company General Electric.

The non-emulsifying crosslinked silicone elastomer may be present in the composition in an active material (solids) content ranging from 0.1% to 2% by weight, relative to the total weight of the composition, preferably from 0.2% to 1% by weight and better still from 0.3% to 0.8% by weight, relative to the total weight of the composition.

The composition according to the invention may also comprise fillers.

The term "fillers" should be understood as meaning colourless or white, mineral or organic particles of any shape, which are insoluble in the medium of the composition, irrespective of the temperature at which the composition is manufactured, and which do not colour the composition.

The fillers may be of any shape, platelet-shaped, spherical or oblong, irrespective of the crystallographic form (for example lamellar, cubic, hexagonal, orthorhombic, etc.). Mention may be made of talc, mica, silica, kaolin, poly-β-alanine and polyethylene, powders of tetrafluoroethylene polymers (Teflon®), lauroyllysine, starch, boron nitride, hollow polymer microspheres such as those of polyvinylidene chloride/acrylonitrile, for instance Expancel® (Nobel Industrie), acrylic acid copolymer microspheres, silicone resin microbeads (for example Tospearls® from Toshiba), polyorganosiloxane elastomer particles, precipitated calcium carbonate, magnesium carbonate, magnesium hydrogen carbonate, hydroxyapatite, barium sulfate, aluminium oxides, polyurethane powders, composite fillers, hollow silica microspheres, and glass or ceramic microcapsules.

The fillers may be present in the composition in a content ranging from 0.1% to 10% by weight, preferably ranging from 0.1% to 8% by weight and preferentially from 0.1% to 5% by weight, relative to the total weight of the composition.

According to one embodiment of the invention, the composition comprises less than 1% by weight of wax, relative to the total weight of the composition, or is even free of wax. The term "wax" is intended to mean a lipophilic compound, which is solid at ambient temperature (25° C.) and atmospheric pressure, with a reversible solid/liquid change of state, having a melting point greater than about 40° C., which may be up to 200° C., and having in the solid state anisotropic crystal organization. In general, the size of the wax crystals is such that the crystals diffract and/or scatter light, giving the composition that comprises them a more or less opaque cloudy appearance. By bringing the wax to its melting point, it is possible to make it miscible with oils and to form a microscopically homogeneous mixture, but if the temperature of the mixture is brought back to ambient temperature, recrystallization of the wax, which is microscopically and macroscopically detectable (opalescence), is obtained.

Advantageously, the emulsion according to the invention has a viscosity, measured at 25° C., at a shear rate of 200 min$^{-1}$ (200 rpm, i.e. a frequency of 50 Hz), ranging from 0.2 to 2.5 Pa·s (2 to 25 poises) and preferably ranging from 1 to 2 Pa·s (10 to 20 poises). The viscosity is measured at 25° C., using a Rheomat 180 viscometer from Mettler, equipped with a No. 3 spindle, the measurement being performed after 10 minutes of rotation of the spindle (after which time stabilization of the viscosity and of the spin speed of the spindle are observed), at a shear rate of 200 min$^{-1}$.

The composition according to the invention is in particular intended for topical, in particular cosmetic or dermatological, use.

In a known manner, the cosmetic or dermatological composition of the invention may also contain adjuvants that are common in the cosmetics or dermatology field, such as UV-screening agents, preserving agents, fragrances, bactericides, odour absorbers, colorants, salts, surfactants, thickeners or bases. The amounts of these various adjuvants are those conventionally used in the field under consideration, for example from 0.01% to 20% of the total weight of the composition. Depending on their nature, these adjuvants can be introduced into the fatty phase or into the aqueous phase.

The composition according to the invention may be applied to the skin, body hair, the eyelashes, the hair, the nails or the lips, according to the use for which it is intended. It may thus be used in a cosmetic treatment process for the skin comprising the application of the composition according to the invention to the skin, for example with a view to toning it, to regenerating it, to smoothing the wrinkles of the skin, and/or for combating skin ageing, for combating the damaging effects of UV radiation and/or for reinforcing skin tissues against attacks from the environment.

As a variant, the composition according to the invention may be used for the manufacture of a dermatological preparation.

The composition may be a care composition, in particular may be a skin care product such as a skin care base, a care cream (day, night, anti-wrinkle cream), a makeup base; a lip care composition (lip balm); or an anti-sun or self-tanning composition.

The composition may also be a makeup composition, in particular a skin makeup composition.

Advantageously, the composition is a leave-on composition.

The emulsion according to the invention can be prepared according to the following general procedure:

Mix the constituents of the aqueous phase while heating at a temperature of approximately 70° C. Mix moreover the oils and the surfactants, heating at a temperature of approximately 80° C. Pour the fatty phase into the aqueous phase, at a temperature of approximately 70° C., then stir for 10 minutes, using a turbine, at high speed. Cool the emulsion obtained to approximately 60° C. Then add the thickeners, then stir again for 10 minutes. Cool to approximately 50° C. Then introduce the salicylic acid or derivative premixed with water, then optionally the other active agents.

The invention will now be illustrated with the aid of the non-limiting examples that follow.

COMPARATIVE EXAMPLES 1 to 6

Face care compositions in the form of an oil-in-water emulsion having the following composition were prepared: Examples 1 and 6 according to the invention and Examples 2 to 5 outside the invention (one of the ingredients of Examples 1 and 6 was deleted).

|  | 1 | 2 | 3 | 4 | 5 | 6 |
|---|---|---|---|---|---|---|
| Mixture of glyceryl monostearate and polyethylene glycol stearate (100 EO) (Arlacel 165 FL from Croda) | 1.8 | 1.8 | — | 1.8 | 1.8 | 1.8 |
| Stearyl alcohol | 0.5 | 0.5 | 0.5 | 0.5 | 0.5 | 0.5 |
| Glyceryl stearate | 1.5 | 1.5 | 1.5 | 1.5 | 1.5 | 1.5 |
| Octyldodecanol | 1 | 1 | 1 | 1 | 1 | 1 |
| Dimethicone (Xiameter PMX-200 Silicone Fluid 5CS from Dow Corning) | 4 | 4 | 4 | 4 | 4 | 4 |
| Hydrogenated polyisobutene (Parleam from NOF Corporation) | 4.5 | 4.5 | 4.5 | 4.5 | 4.5 | 4.5 |
| Isopropyl N-lauroylsarcosinate | 1 | 1 | 1 | 1 | 1 | 1 |
| Mixture of crosslinked polydimethylsiloxane and of polydimethylsiloxane (6 cSt) (24/76) (KSG16 from Shin-Etsu) | 2 | 2 | 2 | 2 | 2 | 2 |
| Salicylic acid | 1.5 | 1.5 | 1.5 | 1.5 | 1.5 | 1.5 |
| Sodium hydroxide | 0.5 | 0.5 | 0.5 | 0.5 | 0.5 | 0.5 |
| Polyacrylamidomethylpropanesulfonic acid partially neutralized with aqueous ammonia and highly cross-linked (Hostacerin AMPS from Clariant) | 1.4 | 1.4 | 1.4 | 1.4 | — | 1.4 |
| Sodium polyacrylate (Cosmedia SP from Cognis) | 0.2 | 0.2 | 0.2 | — | 0.2 | 0.2 |
| EO-PO-EO block copolymer (Synperonic ® PE/F108 from Croda) | 0.5 | — | 0.5 | 0.5 | 0.5 | — |
| EO-PO-EO block copolymer (Synperonic ® PE/L64 from Croda) | — | — | — | — | — | 0.5 |
| Xanthan gum (RhodicareXC from Rhodia) | 0.15 | 0.15 | 0.15 | 0.15 | 0.15 | 0.15 |
| Disodium salt of ethylenediaminetetraacetic acid | 0.3 | 0.3 | 0.3 | 0.3 | 0.3 | 0.3 |
| Glycerol | 5 | 5 | 5 | 5 | 5 | 5 |
| Butylene glycol | 3 | 3 | 3 | 3 | 3 | 3 |
| Ethanol | 3 | 3 | 3 | 3 | 3 | 3 |
| Water | qs 100 | qs 100 | qs 100 | qs 100 | qs 100 | qs 100 |

For each composition, its macroscopic appearance was evaluated at T0 and after storage for 15 days at 55° C. and for 2 months at 45° C. The emulsion was also observed under a microscope on these timings in order to see the homogeneity of the oil globules and the composition was also subjected to centrifugation at 9000 g for 1 hour.

The compositions of Examples 1 and 6 have a viscosity of 0.8 Pa·s (according to the measuring conditions previously described).

The following results were obtained:

|  | Ex 1 | Ex 2 | Ex 3 |
|---|---|---|---|
| Observation T0 | Homogeneous | Not homogeneous | Homogeneous |
| T15 d 55° C. | Homogeneous | Not homogeneous | Not homogeneous |
| T2 months 45° C. | Homogeneous | Not homogeneous | NE |

|  | Ex 4 | Ex 5 | Ex 6 |
|---|---|---|---|
| Observation T0 | Homogeneous | Not homogeneous | Homogeneous |
| T15 d 55° C. | Not homogeneous | Not homogeneous | Homogeneous |
| T2 months 45° C. | NE | Not homogeneous | NE |

NE: not evaluated

These results show that the emulsions of Examples 1 and 6 according to the invention exhibit good stability at T0 and after storage for 15 days at 55° C. Moreover, Example 1 according to the invention is also stable after 2 months at 45° C. When observed under a microscope, the emulsions of Examples 1 and 6 are fine and tight.

The compositions of Examples 1 and 6 are applied to the face by daily use during the daytime.

EXAMPLE 7

A composition similar to that of Example 1, but containing 0.3 g of 5-n-octanoylsalicylic acid in place of 1.5 g of salicylic acid (weight difference compensated for with water), was prepared.

The composition obtained is stable at T0 and after storage for 15 days at 55° C. and also for 2 months at 45° C. The composition has a viscosity at T0 of 0.2 Pa·s (according to the measuring conditions previously described).

The composition of Example 7 is applied to the face by daily use during the daytime.

The invention claimed is:

1. A composition in the form of an oil-in-water emulsion comprising:
    a fatty acid ester of polyethylene glycol;
    a $C_{16}$-$C_{22}$ fatty acid ester of glycerol;
    a polycondensate of ethylene oxide and of propylene oxide constituted of polyethylene glycol and polypropylene glycol blocks;
    an at least partially neutralized acrylic acid homopolymer;
    a 2-acrylamido-2-methylpropanesulfonic acid polymer;
    a salicylic acid compound chosen from salicylic acid and salicylic acid derivatives of formula (I):

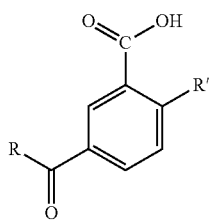

(I)

in which:
  the radical R denotes a linear, branched or cyclic, saturated aliphatic chain containing from 2 to 22 carbon atoms; an unsaturated chain containing from 2 to 22 carbon atoms containing one or more double bonds that may be conjugated; an aromatic nucleus linked to the carbonyl radical directly or via saturated or unsaturated aliphatic chains containing from 2 to 7 carbon atoms; said groups possibly being substituted with one or more substituents, which may be identical or different, chosen from (a) halogen atoms, (b) the trifluoromethyl group, (c) hydroxyl groups in free form or esterified with an acid containing from 1 to 6 carbon atoms, or (d) a carboxyl function in free form or esterified with a lower alcohol containing from 1 to 6 carbon atoms;
  R' is a hydroxyl group;
  and salts thereof derived from an inorganic or organic base,
the composition having a viscosity, measured at 25° C., at a shear rate of 200 min$^{-1}$, of less than or equal to 2.5 Pa·s.

2. The composition according to claim 1, wherein the radical R is a $C_3$-$C_{11}$ alkyl group.

3. The composition according to claim 1, which comprises a salicylic acid compound chosen from salicylic acid or 5-n-octanoylsalicylic acid.

4. The composition according to claim 1, wherein the fatty acid ester of polyethylene glycol is chosen from $C_{16}$-$C_{22}$ fatty acid esters comprising from 8 to 120 ethylene oxide units.

5. The composition according to claim 1, wherein the fatty acid ester of polyethylene glycol is chosen from polyethylene glycol stearates.

6. The composition according to claim 1, wherein the fatty acid ester of polyethylene glycol comprises from 20 to 120 ethylene oxide units.

7. The composition according to claim 1, which comprises a $C_{16}$-$C_{22}$ fatty acid ester of glycerol chosen from glycerol stearates.

8. The composition according to claim 1, which comprises a mixture of glyceryl stearate and of polyethylene glycol 100 EO monostearate.

9. The composition according to claim 1, which comprises a polyethylene glycol/polypropylene glycol/polyethylene glycol triblock polycondensate.

10. The composition according to claim 1, wherein the polycondensate of ethylene oxide and of propylene oxide has a weight-average molecular weight ranging from 1000 to 15000.

11. The composition according to claim 1, wherein the monomer comprising a sulfonic group is 2-acrylamido-2-methylpropanesulfonic acid.

12. The composition according to claim 1, wherein the homopolymer of a monomer comprising a sulfonic group is a crosslinked and neutralized 2-acrylamido-2-methylpropanesulfonic acid homopolymer.

13. The composition according to claim 1, wherein the homopolymer of a monomer comprising a sulfonic group is present in a content ranging from 0.1% to 3% by weight relative to the total weight of the composition.

14. The composition according to claim 1, wherein the acrylic acid homopolymer is sodium polyacrylate.

15. The composition according to claim 1, wherein the at least partially neutralized acrylic acid homo-polymer is present in a content ranging from 0.05% to 1% by weight, relative to the total weight of the composition.

16. The composition according to claim 1, which comprises water in a content ranging from 40% to 95% by weight, relative to the total weight of the composition.

17. The composition according to claim 1, which comprises oil in a content ranging from 1% to 50% by weight, relative to the total weight of the composition.

18. The composition according to claim 1, which comprises a non-emulsifying crosslinked organopolysiloxane elastomer (also called crosslinked silicone elastomer).

19. The composition according to claim 1, which comprises at least one cosmetic or dermatological adjuvant chosen from UV-screening agents, fillers, preserving agents, fragrances, bactericides, odour absorbers, colorants, salts, surfactants, thickeners and bases.

20. The composition according to claim 1, which has a viscosity, measured at 25° C., at a shear rate of 200 min$^{-1}$, ranging from 0.2 to 2.5 Pa·s.

21. A non-therapeutic process for caring for and/or making up keratin materials, comprising the application to the keratin materials of a composition according to claim 1.

22. The composition according to claim 1, which has a viscosity, measured at 25° C., at a shear rate of 200 min$^{-1}$, ranging from 1 to 2 Pa·s.

23. The composition according to claim 1, wherein the at least partially neutralized acrylic acid homopolymer is present in a content ranging from 0.05% to 1% by weight, relative to the total weight of the composition and the 2-acrylamido-2-methylpropanesulfonic acid polymer is present in a content ranging from 0.1% to 3% by weight relative to the total weight of the composition.

24. The composition according to claim 23, wherein fatty acid ester of polyethylene glycol is present in a content ranging from 0.1% to 10% by weight relative to the total weight of the composition; the $C_{16}$-$C_{22}$ fatty acid ester of glycerol is present in a content ranging from 0.1% 10% by weight relative to the total weight of the composition; the polycondensate of ethylene oxide and of propylene oxide constituted of polyethylene glycol and polypropylene glycol blocks is present in a content ranging from 0.01% to 5% by weight relative to the total weight of the composition and the salicylic acid compound is present in a content ranging from 0.05% to 10% by weight relative to the total weight of the composition.

* * * * *